United States Patent
Wei et al.

(10) Patent No.: US 10,219,726 B2
(45) Date of Patent: Mar. 5, 2019

(54) GAIT ANALYSIS SYSTEM AND METHOD THEREOF

(71) Applicant: INSTITUTE FOR INFORMATION INDUSTRY, Taipei (TW)

(72) Inventors: Shih-Yao Wei, Taipei (TW); Chih-Chun Ma, Taoyuan (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 187 days.

(21) Appl. No.: 15/224,682

(22) Filed: Aug. 1, 2016

(65) Prior Publication Data
US 2017/0238845 A1  Aug. 24, 2017

(30) Foreign Application Priority Data

Feb. 19, 2016  (TW) .............................. 105104972 A

(51) Int. Cl.
*A61B 5/11* (2006.01)
*A61B 5/103* (2006.01)
*A61B 5/00* (2006.01)
*G09B 19/00* (2006.01)
*A61B 5/107* (2006.01)

(52) U.S. Cl.
CPC ............ *A61B 5/112* (2013.01); *A61B 5/1036* (2013.01); *A61B 5/1038* (2013.01); *A61B 5/1071* (2013.01); *A61B 5/1122* (2013.01); *A61B 5/6828* (2013.01); *A61B 5/6829* (2013.01); *A61B 5/7278* (2013.01); *G09B 19/003* (2013.01); *A61B 5/1072* (2013.01);
(Continued)

(58) Field of Classification Search
USPC ...................................................... 434/255
See application file for complete search history.

(56) References Cited

U.S. PATENT DOCUMENTS

2012/0226364 A1  9/2012  Kampas et al.

FOREIGN PATENT DOCUMENTS

EP  1649984 A1  4/2006
TW  201114408 A  5/2011
(Continued)

OTHER PUBLICATIONS

The extended search report of the corresponding European application dated May 19, 2017.
(Continued)

*Primary Examiner* — Kesha Frisby
(74) *Attorney, Agent, or Firm* — CKC & Partners Co., LLC

(57) ABSTRACT

A gait analysis system includes a foot sensing unit, a knee sensing unit and a portable device. The foot sensing unit senses pressure information. The knee sensing unit senses first and second three-dimensional rotational attributes of knee. The portable device generates direction of ground reaction force according to the pressure information, the first and the second three-dimensional rotational attributes of knee and a model of direction of ground reaction force, generates knee moment according to the pressure information, the first and the second three-dimensional rotational attribute of knee, the direction of ground reaction force, length of tibia and model of knee moment, determines gait information according to a gait model and one of the pressure information, the first and the second three-dimensional rotational attributes of knee, and generates gait analysis result according to the gait information, the knee moment and the gait model.

19 Claims, 11 Drawing Sheets

(52) U.S. Cl.
CPC .......... *A61B 5/4528* (2013.01); *A61B 5/4585* (2013.01); *A61B 2562/0219* (2013.01)

(56) References Cited

FOREIGN PATENT DOCUMENTS

| | | |
|---|---|---|
| TW | 201118627 A | 6/2011 |
| TW | 201233382 A | 8/2012 |
| WO | 2015164706 A1 | 10/2015 |

OTHER PUBLICATIONS

Josien C. van den Noort et al,"The knee adduction moment measured with an instrumented force shoe in patients with knee osteoarthritis"(p. 281-288, Journal of Biomechanics, Jan. 10, 2012, Publisher: Elsevier).
The office action of the corresponding Taiwan application dated Dec. 20, 2016.

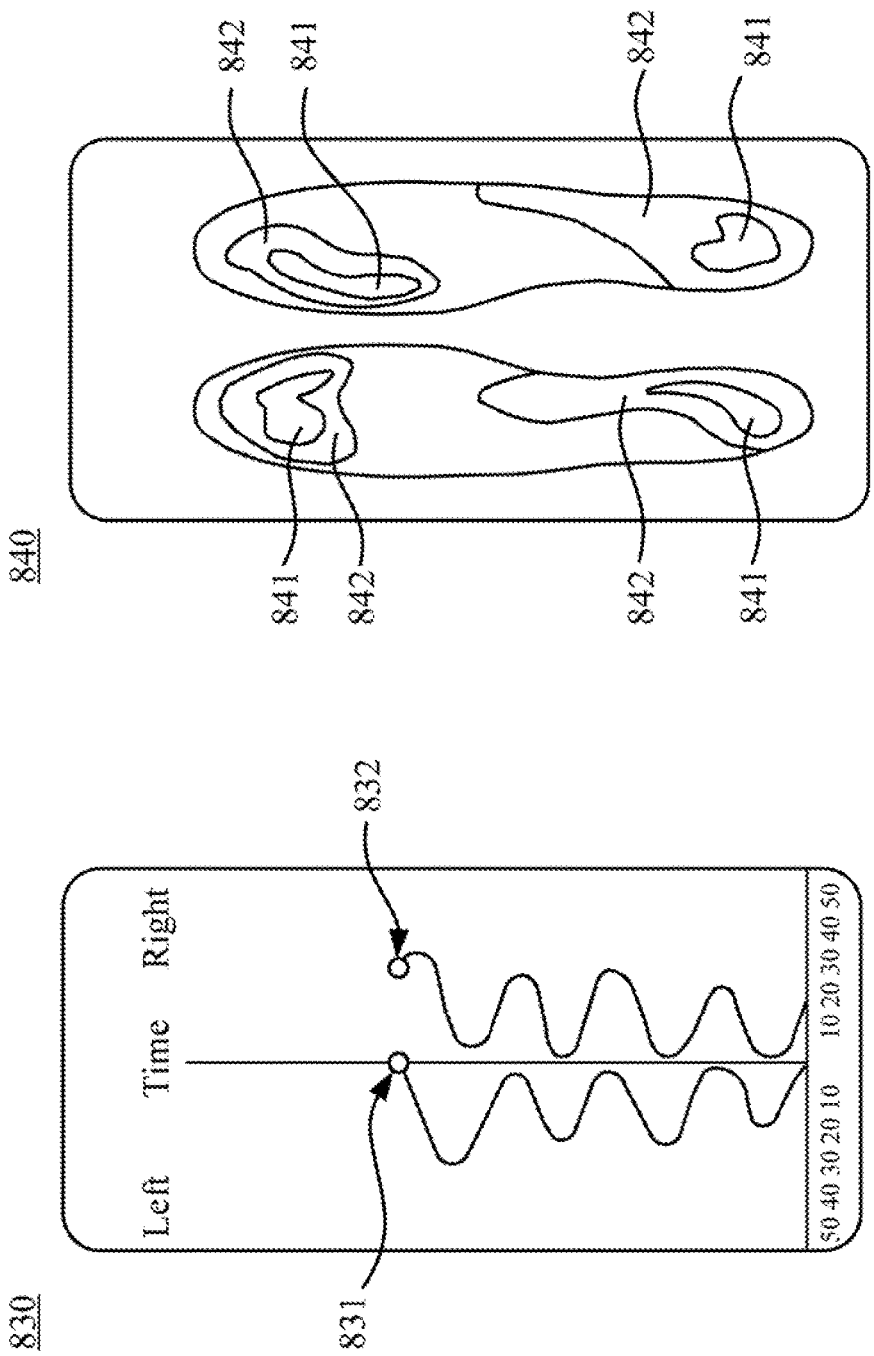

GAIT ANALYSIS SYSTEM AND METHOD THEREOF

RELATED APPLICATIONS

This application claims priority to Taiwan Application Serial Number 105104972, filed Feb. 19, 2016, which is herein incorporated by reference.

BACKGROUND

Technical Field

The present invention relates to an analysis technology. More particularly, the present invention relates to a gait analysis system and a method thereof.

Description of Related Art

Because of an aged society, knee osteoarthritis (knee OA) problems become serious gradually, and seriously affect human health and quality of life. Moreover, because doing exercise becomes popular recently, people between ages of 30 to 40 may also suffer from the knee OA. Knee OA not only results in problems of walking function, but also affects human health.

In reasons of forming knee OA, non-uniform cartilage wear and unbalanced reproducing speed caused by an inappropriate gait and damage of medial sides of knee joints and femur caused by an extra-large bending angle of knee are common reasons. Therefore, adjusting to a correct gait is a solution to maintain healthy knee joints.

SUMMARY

The present disclosure provides a gait analysis system that includes a foot sensing unit, a knee sensing unit and a portable device. The foot sensing unit includes at least one pressure sensing unit that is configured to sense pressure information. The knee sensing unit includes a first inertial sensing unit that is configured to sense a first three-dimensional rotational attribute of knee and a second inertial sensing unit that is configured to sense a second three-dimensional rotational attribute of knee. The portable device is configured to generate direction of ground reaction force according to the pressure information, the first three-dimensional rotational attribute of knee, the second three-dimensional rotational attribute of knee and a model of direction of ground reaction force, to generate a knee moment according to the pressure information, the first three-dimensional rotational attribute of knee, the second three-dimensional rotational attribute of knee, the direction of ground reaction force, a length of tibia and a model of knee moment, to determine gait information according to a gait model and one of the pressure information, the first three-dimensional rotational attribute of knee and the second three-dimensional rotational attribute of knee, and to generate a gait analysis result according to the gait information, the knee moment and the gait model.

In an embodiment of the present disclosure, wherein the portable device displays the gait analysis result through a user interface. The gait analysis result includes distribution information of knee force.

In an embodiment of the present disclosure, wherein the first three-dimensional rotational attribute of knee includes a tibia angle, and the second three-dimensional rotational attribute of knee includes a femur angle. The portable device is further configured to generate knee angle information according to the tibia angle and the femur angle, and to display the knee angle information through the user interface.

In an embodiment of the present disclosure, wherein the portable device further stores a foot parameter and is configured to determine a sequence of the knee moment and the knee angle information for determination according to the foot parameter and the gait information to generate a gait adjustment advice, and to display the gait adjustment advice through the user interface.

In an embodiment of the present disclosure, wherein the foot sensing unit further includes at least one inertial sensing unit that is configured to sense an acceleration and an angle of foot. The portable device is further configured to generate a foot progression angle, a step length and a step width according to the acceleration and the angle of foot.

In an embodiment of the present disclosure, wherein the model of direction of ground reaction force includes a model of center of pressure. The portable device is further configured to generate a center of foot pressure information according to the pressure information and the model of center of pressure, and to display the center of foot pressure information through a user interface.

In an embodiment of the present disclosure, wherein the portable device is further configured to generate a center of gravity correction advice according to the center of foot pressure information, and to display the center of gravity correction advice through the user interface.

In an embodiment of the present disclosure, wherein the portable device is further configured to receive the model of direction of ground reaction force, the model of knee moment and the gait model from an analysis engine. The analysis engine builds the model of direction of ground reaction force, the model of knee moment and the gait model through machine learning.

In an embodiment of the present disclosure, the gait analysis system further includes a support unit that includes a support pressure sensing unit and a support inertial sensing unit and is configured to generate support pressure data and a support angle data. The support unit and the foot sensing unit are further configured to generate a relative position of the foot sensing unit and the support unit. The portable device is further configured to calculate a support weight according to the support pressure data and the support angle data, and to display the support weight and the relative position through a user interface.

Another aspect of the present disclosure provides a gait analysis system that includes a foot sensing unit, a knee sensing unit, an analysis engine and a portable device. The foot sensing unit includes at least one pressure sensing unit that is configured to sense a pressure information. The knee sensing unit includes a first inertial sensing unit that is configured to sense a first three-dimensional rotational attribute of knee and a second inertial sensing unit that is configured to sense a second three-dimensional rotational attribute of knee. The analysis engine is configured to build a model of direction of ground reaction force, a model of knee moment and a gait model through machine learning. The portable device is configured to receive the pressure information, the first three-dimensional rotational attribute of knee and the second three-dimensional rotational attribute of knee from the foot sensing unit and the knee sensing unit, and to send the pressure information, the first three-dimensional rotational attribute of knee and the second three-dimensional rotational attribute of knee to the analysis engine. The analysis engine is configured to generate a direction of ground reaction force according to the pressure information, the first three-dimensional rotational attribute of knee, the second three-dimensional rotational attribute of knee and the model of direction of ground reaction force, to generate a knee moment according to the pressure information, the first three-dimensional rotational attribute of knee, the second three-dimensional rotational attribute of knee, the direction of ground reaction force, a length of tibia and the model of knee moment, to determine a gait information according to the gait model and one of the pressure information, the first three-dimensional rotational attribute of knee and the second three-dimensional rotational attribute of knee, to generate a gait analysis result according to the gait information, the knee moment and the gait model, and to send the gait analysis result to the portable device.

In an embodiment of the present disclosure, wherein the first three-dimensional rotational attribute of knee includes a tibia angle, and the second three-dimensional rotational attribute of knee includes a femur angle. The analysis engine is further configured to generate knee angle information according to the tibia angle and the femur angle, and to send the knee angle information to the portable device. The portable device is further configured to display the knee angle information through a user interface.

In an embodiment of the present disclosure, wherein the foot sensing unit further includes at least one inertial sensing unit that is configured to sense an acceleration and an angle of foot. The analysis engine is further configured to generate a foot progression angle, a step length and a step width according to the acceleration and the angle of foot.

In an embodiment of the present disclosure, wherein the model of direction of ground reaction force includes a model of center of pressure. The analysis engine is further configured to generate a center of foot pressure information according to the pressure information and the model of center of pressure, and to send the center of foot pressure information to the portable device. The portable device is further configured to display the center of foot pressure information through a user interface.

In an embodiment of the present disclosure, the gait analysis system further includes a support unit that includes a support pressure sensing unit and a support inertial sensing unit and is configured to generate support pressure data and support angle data. The support unit and the foot sensing unit are further configured to generate a relative position of the foot sensing unit and the support unit and to send the relative position to the analysis engine. The analysis engine is further configured to calculate a support weight according to the support pressure data and the support angle data, and to send the support weight to the portable device. The portable device is further configured to display the support weight and the relative position through a user interface.

Another aspect of the present disclosure provides a gait analysis method that includes steps as follows. A pressure information is sensed by a foot sensing unit. A first three-dimensional rotational attribute of knee and a second three-dimensional rotational attribute of knee are sensed by a knee sensing unit. A direction of ground reaction force is generating by a portable device according to the pressure information, the first three-dimensional rotational attribute of knee, the second three-dimensional rotational attribute of knee and a model of direction of ground reaction force. A knee moment is generated by the portable device according to the pressure information, the first three-dimensional rotational attribute of knee, the second three-dimensional rotational attribute of knee, the direction of ground reaction force, a length of tibia and a model of knee moment. A gait information is determined by the portable device according to a gait model and one of the pressure information. the first three-dimensional rotational attribute of knee and the second three-dimensional rotational attribute of knee. A gait analysis result is generated by the portable device according to the gait information, the knee moment and the gait model.

In an embodiment of the present disclosure, knee angle information is generated by the portable device according to a tibia angle and a femur angle. The first three-dimensional rotational attribute of knee includes the tibia angle; the second three-dimensional rotational attribute of knee comprises the femur angle. The knee angle information is displayed by a user interface of the portable device.

In an embodiment of the present disclosure, acceleration and an angle of foot are sensed by at least one inertial sensing unit of the foot sensing unit. A foot progression angle, a step length and a step width are generated by the portable device according to the acceleration and the angle of foot. A center of foot pressure information is generated according to the pressure information and a model of center of pressure of the model of direction of ground reaction force by the portable device. The center of foot pressure information is displayed by a user interface of the portable device.

In an embodiment of the present disclosure, the model of direction of ground reaction force, the model of knee moment and the gait model are built by an analysis engine through machine learning. The model of direction of ground reaction force, the model of knee moment and the gait model are received from the analysis engine by the portable device.

In an embodiment of the present disclosure, support pressure data and support angle data are generated by a support unit. the support unit includes a support pressure sensing unit and a support inertial sensing unit. A relative position of the foot sensing unit and the support unit is generated by the support unit and the foot sensing unit. A support weight is calculated by the portable device according to the support pressure data and the support angle data. The support weight and the relative position are displayed by a user interface of the portable device.

In conclusion, the gait system and the gait method of the present disclosure can sense pressure data and angle data of a user's foot and knee, and generate an analysis result and an advice for adjustment after analysis. The portable device held by the user can display the analysis result and the advice for adjustment, and therefore the user can understand whether the current gait is harmful to health immediately and adjust to a gait that is beneficial to health according to the advice for adjustment.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIGS. 8A-8E are flow charts of user interfaces according to some embodiments of the present disclosure.

DETAILED DESCRIPTION

In order to make the description of the disclosure more detailed and comprehensive, reference will now be made in detail to the accompanying drawings and the following embodiments. However, the provided embodiments are not used to limit the ranges covered by the present disclosure; orders of step description are not used to limit the execution sequence either. Any devices with equivalent effect through rearrangement are also covered by the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof Unless otherwise indicated, all numbers expressing quantities, conditions, and the like in the instant disclosure and claims are to be understood as modified in all instances by the term "about." The term "about" refers, for example, to numerical values covering a range of plus or minus 20% of the numerical value. The term "about" preferably refers to numerical values covering range of plus or minus 10% (or most preferably, 5%) of the numerical value. The modifier "about" used in combination with a quantity is inclusive of the stated value.

Figure 1:
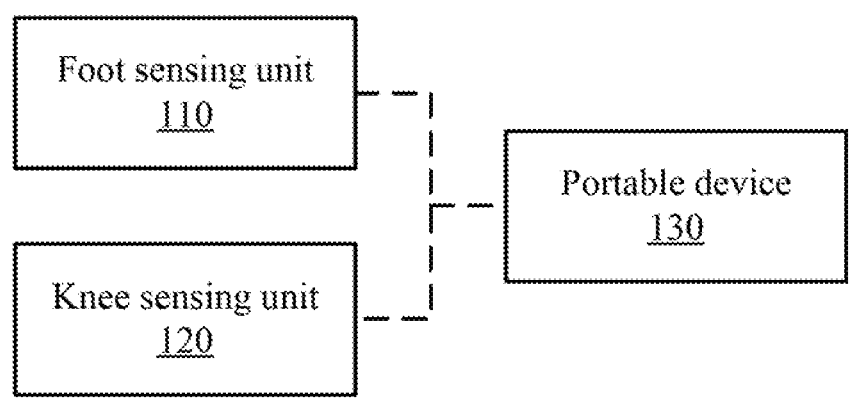
FIG. 1 is a schematic diagram of a gait analysis system according to an embodiment of the present disclosure.

FIG. 1 is a schematic diagram of a gait analysis system 100 according to an embodiment of the present disclosure. The gait analysis system 100 includes a foot sensing unit 110, a knee sensing unit 120 and a portable device 130. In order to collect sensing data of a user's foots and knees, the portable device 130 can be establish wireless connection (e.g., bluetooth, bluetooth low energy (BLE), WiFi, ZigBee, near field communication (NFC), infrared or another short-distance wireless communication technology) with the foot sensing unit 110 and the knee sensing unit 120. The portable device 130 stores a model of direction of ground reaction force, a model of knee moment (KM) and a gait model for analyzing a gait of a user. In an embodiment, the gait model may include a model of gait situation and a gait analysis model. The model of gait situation is used to generate gait information of the user (e.g., walking on level ground or going upstairs). The gait analysis model is used to generate a gait analysis result (e.g., distribution information of knee force and gait information).

Alternatively, in another embodiment, the model of gait situation and the gait analysis model are respectively generated as two independent models and stored in the portable device 130.

Figure 2:
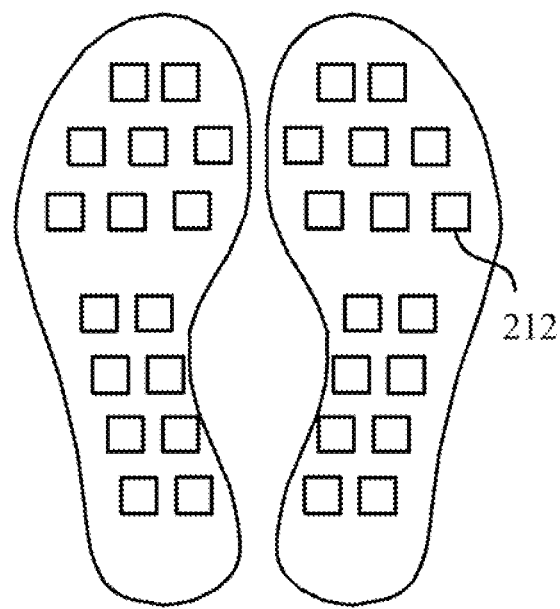
FIG. 2 is a schematic diagram of a foot sensing unit according to an embodiment of the present disclosure.

In an embodiment, as shown in FIG. 2, the foot sensing unit 110 includes a pressure sensing unit 212 (e.g., a pressure sensor), and is attached on sole of the user. For example, the foot sensing unit 110 is attached in shoes, on shoe insoles or other supplies or devices adaptable for foots. When the user walks, the foot sensing unit 110 may detect pressure information (e.g., pressure data on different positions of the user's sole) of the user's sole through the pressure sensor and send the pressure information to the portable device 130 for subsequent analysis.

Figure 3:
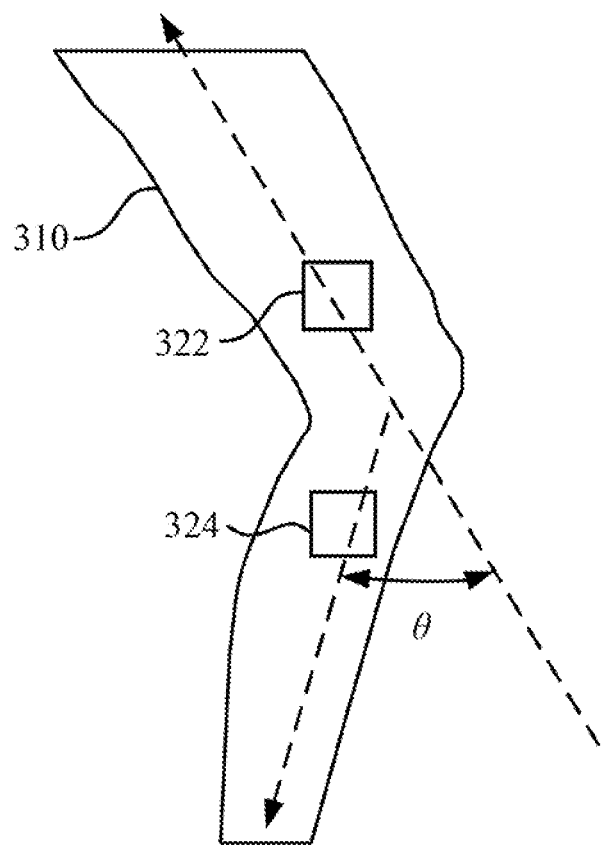
FIG. 3 is a schematic diagram of a knee sensing unit according to an embodiment of the present disclosure.

In an embodiment, as shown in FIG. 3, the knee sensing unit 120 includes inertial sensing units (IMU) 322 and 324 are attached on positions of the user's tibia and femur, respectively. In a preferable embodiment, the inertial sensing units may be attached in knee braces and located on positions that are respectively on and under the user's knee which are corresponding to the user's tibia and femur. The knee sensing unit 120 may include two inertial sensing units, such as a first inertial sensing unit and a second inertial sensing unit, which are respectively configured to sense first three-dimensional rotational attributes (e.g., tibia angle) of knees and second three-dimensional rotational attributes (e.g., a femur angle) of knees, and send the first three-dimensional rotational attributes and the second three-dimensional rotational attributes to the portable device 130 for subsequent analysis. It should be noted that, according different attached positions of the inertial sensing unit, the first three-dimensional rotational attribute of knee and the second three-dimensional rotational attribute of knee of the present disclosure may be three-dimensional angle information on basis of a human body and not limited to the tibia angle and the femur angle. The three-dimensional angle information on basis of a human body is defined as three-axis rotation angles that are orthogonal to a sagittal plane, a frontal plane and a transverse plane of the human body.

In an embodiment, the foot sensing unit 110 may be integrated in shoe insoles, and the knee sensing unit 120 may be integrated in knee braces so as to be convenient for the user to wear in daily life.

After the portable device 130 receives the pressure information, the first three-dimensional rotational attribute of knee and the second three-dimensional rotational attribute of knee, the portable device 130 can generate the direction of ground reaction force (e.g., direction of ground reaction force vector $\overline{GRF}$) according to the pressure information. the first three-dimensional rotational attribute of knee, the second three-dimensional rotational attribute of knee and the model of direction of ground reaction force.

Then, the portable device 130 generates a knee moment according to the pressure information, the first three-dimensional rotational attribute of knee, the second three-dimensional rotational attribute of knee, the direction of ground reaction force information, the length of tibia and the model of knee moment. Specifically, the portable device 130 first generates a vector r that is from knee to foot according to the user's length of tibia, the first three-dimensional rotational attribute of knee and the second three-dimensional rotational attribute of knee sensed by the knee sensing unit 120. The portable device 130 then generates knee moment KM through the model of knee moment and according to the pressure information (e.g., magnitude of the ground reaction force vector $\overline{GRF}$), the direction of ground reaction force information (e.g., direction of the ground reaction force vector $\overline{GRF}$) and the vector $\bar{r}$ that is from knee to foot. For example, the knee moment KM can be calculated through a formula as follows.

$$KM = \bar{r} \times \overline{GRF}$$

The portable device 130 determines the gait information (e.g., walking on level ground or go upstairs) according to the gait model (or the model of gait situation) and one of the pressure information, the first three-dimensional rotational attribute of knee and the second three-dimensional rotational attribute of knee. Specifically, the pressure information, the first three-dimensional rotational attribute of knee and the second three-dimensional rotational attribute of knee may be used to generate the model of gait situation through a machine learning method. The portable device 130 one of the pressure information, the first three-dimensional rotational attribute of knee and the second three-dimensional rotational attribute of knee collected by the foot sensing unit 110 and the knee sensing unit 120 are substituted into the model of gait situation to determine a gait situation. The portable device 130 then generates the gait analysis result according to the gait information, the knee moment and the gait model (or the gait analysis model). In an embodiment, the portable device 130 displays the gait analysis result through a user interface, and thus the user can know whether the current gait is harmful to knee joints.

In an embodiment, the portable device 130 is further configured to generate knee angle information θ (e.g., bend angles of knee joint) according to the first three-dimensional rotational attribute of knee (e.g., a tibia angle) and the second three-dimensional rotational attribute of knee (e.g., a femur angle), and to display the knee angle information θ of the user's foot 310 though the user interface. As a result, the user can know whether the knee angles of the current gait are in a knee angle range of a correct gait.

In an embodiment, the foot sensing unit 110 further includes at least one inertial sensing unit that is configured to sense acceleration and an angle of foot. The portable device 130 is further configured to generate the user's current foot progression angle, step length and step width according to the acceleration and the angle of foot as a reference to adjust the gait.

In order to effectively correct the user's gait, the portable device 130 is further configured to determine a sequence of the knee moment and the knee angle information for determination according to the gait information to generate a gait correction advice, and to display the gait correction advice through the user interface. Therefore, the user can adjust the current gait to a correct gait according to the gait correction advice.

For example, when the gait information indicates that the user walks on level ground, the sequence for determination is that the knee moment is prior to the knee angle information. The gait correction advice may be a toe angle range from −30 degrees to +45 degrees, an upper limit of the step length is 60 cm, and an upper limit of the knee angle is 30 degrees. When the user walks on level ground and doesn't meet any of the above requirements, the portable device 130 displays a gait correction advice of the unmet requirement through the user interface to remind the user.

Alternatively, when the gait information indicates that the user goes upstairs, the sequence for determination is that the knee angle information is prior to the knee moment. The gait correction advice may be a toe angle range from −20 degrees to +30 degrees, an upper limit of the step width is 30 cm, and an upper limit of the knee angle is 70 degrees. When the user goes upstairs and doesn't meet any of the above requirements, the portable device 130 displays a gait correction advice of the unmet requirement through the user interface to remind the user.

In another embodiment, the model of the direction of ground reaction force includes a model of center of pressure.

The portable device 130 is further configured to generate center of foot pressure information according to the pressure information sensed by the foot sensing unit 110 and the model of center of pressure, and to display the center of foot pressure information through the user interface. In an embodiment, the portable device is further configured to generate center of gravity correction advice according to the center of foot pressure information, and to display the center of gravity correction advice through the user interface. As a result, the user can know center of gravity position in the sole and the center of gravity correction advice when walking to adjust the gait immediately.

Figure 4:
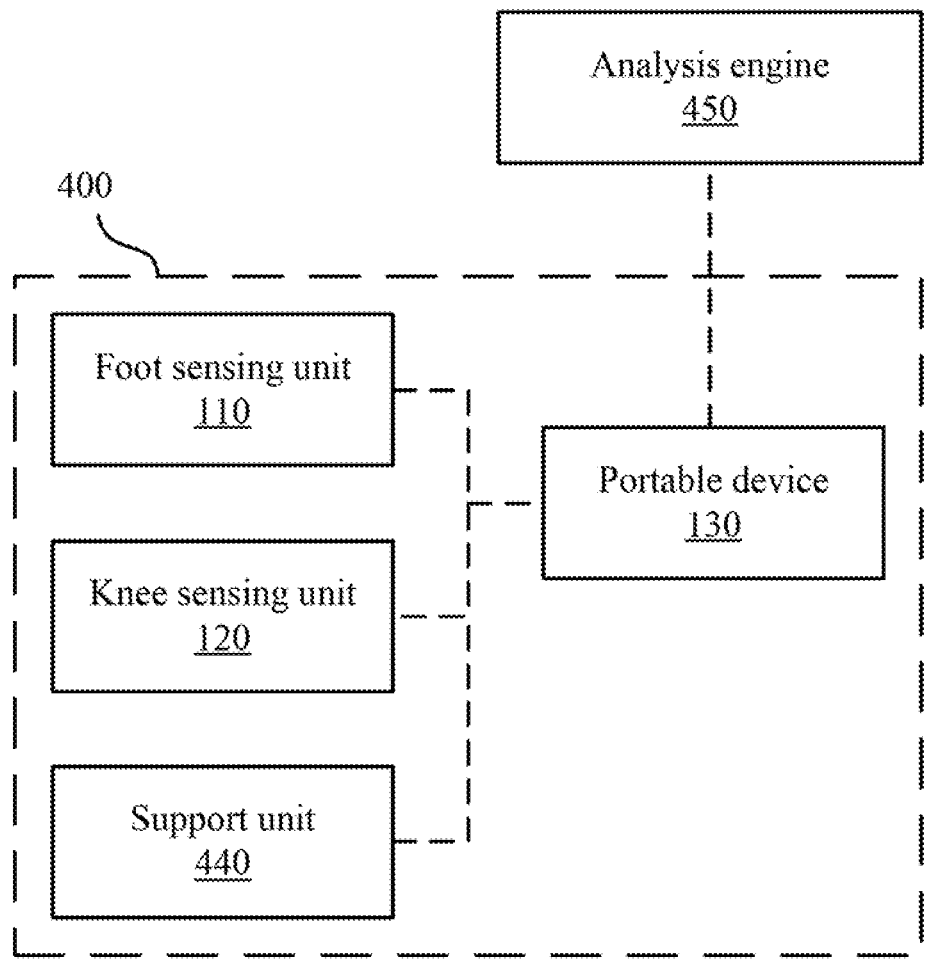
FIG. 4 is a schematic diagram of a gait analysis system according to an embodiment of the present disclosure.
Figure 5:
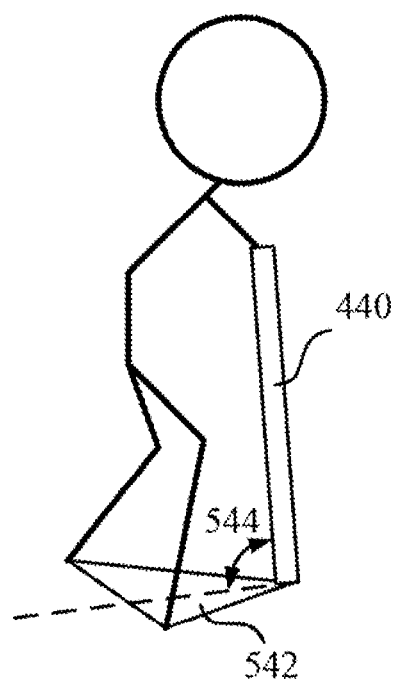
FIG. 5 is a schematic diagram of a support unit according to an embodiment of the present disclosure.

FIG. 4 is a schematic diagram of a gait analysis system 400 according to an embodiment of the present disclosure. The gait analysis system 400 has substantially the same configuration as the gait analysis system 100, except for a support unit 440. The support unit 440 includes a support pressure sensing unit (e.g., a pressure sensor) and a support inertial sensing unit (e.g., an inertial sensing unit (IMU)). The support unit 440 is configured to generate support pressure data and support angle data (e.g., an angle 544 as shown in FIG. 5), and to send to the support pressure data and the support angle data to the portable device 130. The portable device 130 is further configured to calculate a support weight according to the support pressure data and the support angle data, and to display the support weight through the user interface. The support weight indicates a relieved knee joint load when the user uses the support unit 440. The support unit 440 may be implemented in a shape of a cane to assist the user in walking. However, the present disclosure is not limited to the embodiment.

In an embodiment, as shown in FIG. 5, the user uses the support unit 440 and the foot sensing unit 110. The support unit and the foot sensing unit are further configured to generate a relative position of the foot sensing unit and the support unit, and the relative position is shown as an area 542. When the area 542 is more approximate to an equilateral triangle, it indicates that a gait of the user has a higher stability. The portable device 130 may display the relative position (e.g., area 542) through the user interface, and therefore the user can know whether the support unit 440 and feet that wear the foot sensing unit 110 are approximate to a stable position.

In an embodiment, the analysis engine 450 builds the model of direction of ground reaction force, the model of knee moment and the gait model through machine learning. It should be noted that the gait model (including the model of gait situation and the gait analysis model) may execute a personalized adjustment according to foot parameters (e.g., leg type, foot arch) of the user. As a result, the portable device 130 can generate a more accurate gait analysis result through the gait model.

In an embodiment, the portable device 130 may generate activity history information of the user according to the gait information and the gait analysis result and display the activity history information of the user through the user interface. For example, the activity history information includes a step count, calories consumption, a ratio of different gait information (e.g., going upstairs, going downstairs, walking on level ground). As a result, the user may refer to the activity history information to adjust activity pattern (e.g., climbing stairs as frequently as possible to achieve a purpose of consuming excess energy).

Figure 6:
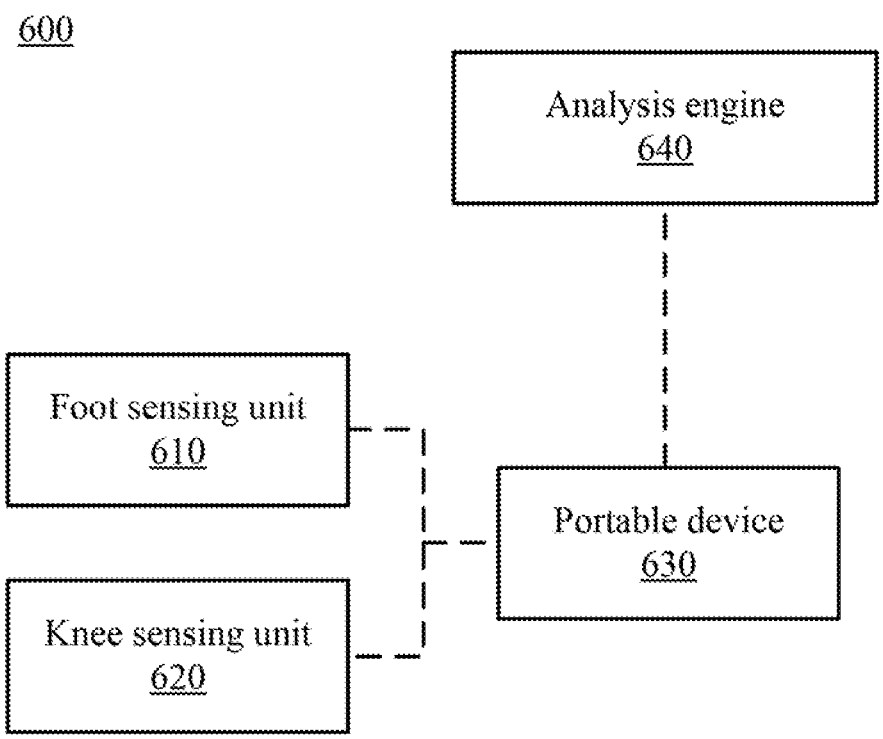
FIG. 6 is a schematic diagram of a gait analysis system according to an embodiment of the present disclosure.

The gait analysis systems 100 and 400 receive the sensing data and process to generate the analysis result and an advice through the portable device 130. In order to describe different implementations of the gait analysis system, reference is made to FIG. 6. FIG. 6 is a schematic diagram of a gait analysis system 600 according to an embodiment of the present disclosure. The gait analysis system 600 includes a foot sensing unit 610, a knee sensing unit 620, a portable device 630 and an analysis engine 640. The analysis engine 640 builds a model of direction of ground reaction force, a model of knee moment and a gait model through machine learning, and stores the model of direction of ground reaction force, the model of knee moment and the gait model in the analysis engine 640. It should be noted that the gait model (including a model of gait situation and a gait analysis model) may execute a personalized adjustment according to foot parameters (e.g., leg type, foot arch) of the user. Operation of the foot sensing unit 610 and the knee sensing unit 620 are similar to above description, and are not repeated herein.

The portable device 630 is configured to receive the pressure information, the first three-dimensional rotational attribute of knee and the second three-dimensional rotational attribute of knee from the foot sensing unit 610 and the knee sensing unit 620, and to send the pressure information, the first three-dimensional rotational attribute of knee and the second three-dimensional rotational attribute of knee to the analysis engine 640. The analysis engine 640 is configured to generate a direction of ground reaction force according to the pressure information, the first three-dimensional rotational attribute of knee, the second three-dimensional rotational attribute of knee and the model of direction of ground reaction force. The analysis engine 640 then generates a knee moment according to the pressure information, the first three-dimensional rotational attribute of knee, the second three-dimensional rotational attribute of knee, the direction of ground reaction force, a tibia length and the model of knee moment. The analysis engine 640 determines gait information according to the gait model and one of the pressure information, the first three-dimensional rotational attribute of knee and the second three-dimensional rotational attribute of knee. The analysis engine 640 generates a gait analysis result according to the gait information, the knee moment and the gait model, and sends the gait analysis result to the portable device 630. In an embodiment, the portable device 640 displays the gait analysis result through a user interface. The gait analysis result includes distribution information of knee force and the gait information.

In an embodiment, the first three-dimensional rotational attribute of knee includes a tibia angle, and the second three-dimensional rotational attribute of knee includes a femur angle. The analysis engine 640 is further configured to generate knee angle information θ according to the tibia angle and the femur angle and to send the knee angle information to the portable device 630. The portable device 630 is further configured to display the knee angle information θ through the user interface.

In an embodiment, the analysis engine 640 is further configured to determine a sequence of the knee moment and the knee angle information for determination according to the gait information to generate a gait correction advice, and to send the gait correction advice to the portable device 630. The portable device 630 is further configured to display the gait correction advice through the user interface. Method of generating the gait correction advice is similar to the above description, and is not repeated herein.

In an embodiment, the model of direction of ground reaction force includes a model of center of pressure. The analysis engine 640 is further configured to generate center of foot pressure information according to the pressure information and the model of center of pressure, and to send the center of foot pressure information to the portable device 630. The analysis engine 640 is further configured to generate a center of gravity correction advice according to the center of foot pressure information, and to send the center of gravity correction advice to the portable device 630. The portable device 630 is further configured to display the center of foot pressure information and the center of gravity correction advice through the user interface.

In an embodiment, the analysis engine 640 is further configured to generate activity history information according to the gait information and the gait analysis result, and to send the activity history information to the portable device 630. The portable device 630 is further configured to display the activity history information through the user interface.

Figure 7:
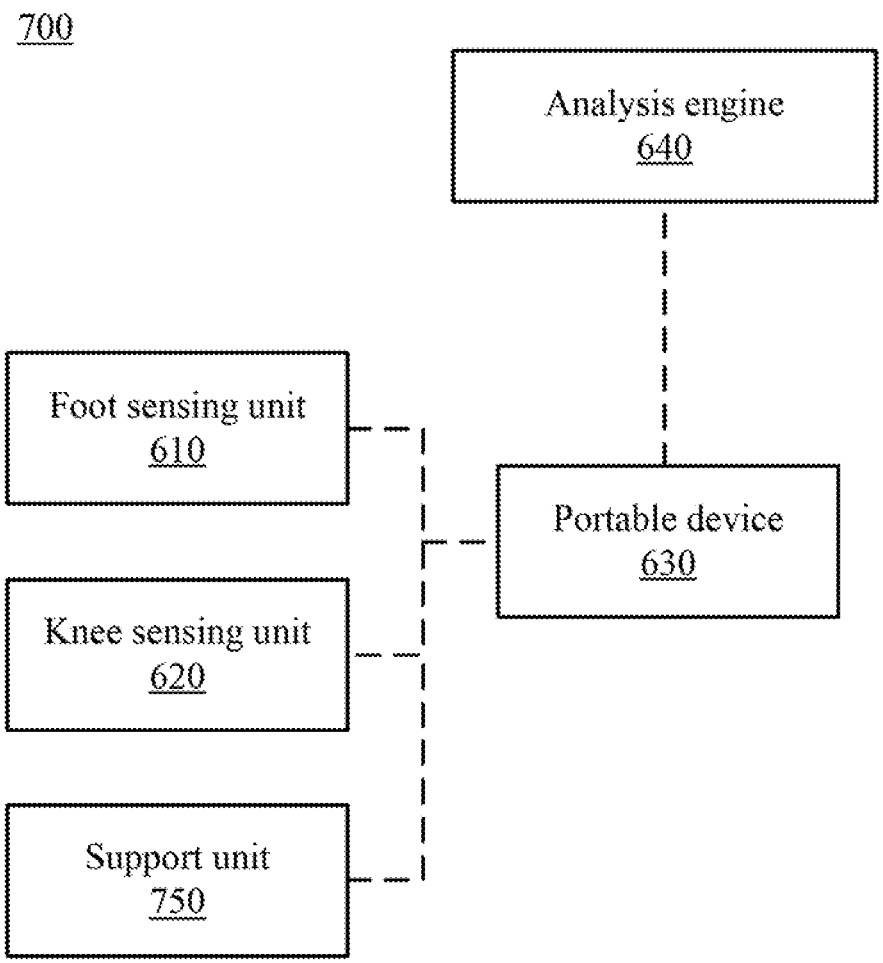
FIG. 7 is a schematic diagram of a gait analysis system according to an embodiment of the present disclosure.

FIG. 7 is a schematic diagram of a gait analysis system 700 according to an embodiment of the present disclosure. The gait analysis system 700 has substantially the same configuration as the gait analysis system 600, except for a support unit 750. Similar to the support unit 440, the support unit 750 includes a support pressure sensing unit (e.g., a pressure sensor) and a support inertial sensing unit (e.g., an inertial sensing unit (IMU)). The support unit 750 is configured to generate support pressure data and support angle data (e.g., an angle 544 as shown in FIG. 5), and to send the support pressure data and the support angle data to the portable device 630. The portable device 630 is further configured to receive the support weight information and a relative position from the support unit 750, and to send the support weight information and the relative position to the analysis engine 640. The analysis engine 640 is further configured to calculate a support weight according to the support pressure data and the support angle data, and to send the support weight to the portable device 630. The portable device 630 is further configured to display the support weight through the user interface. The support weight indicates a relieved knee joint load when the user uses the support unit 440. Methods of sensing and displaying the relative position are similar to the above description, and are not repeated herein.

Different from the gait analysis systems 100 and 400, the gait analysis systems 600 and 700 both receive the sensing data through the portable device 630 and send the sensing data to the analysis engine 640. The analysis engine 640 processes the sensing data to generate the analysis result and the advice, and send the analysis result and the advice to the portable device 630. The portable device 630 can display the analysis result and the advice through the user interface without needing to execute complicated process and calculation.

In order to describe implementation of the user interface, reference is made to FIGS. 8A-8E. FIGS. 8A-8E are flow charts of user interfaces 810-850 according to some embodiments of the present disclosure.

Figure 8A:
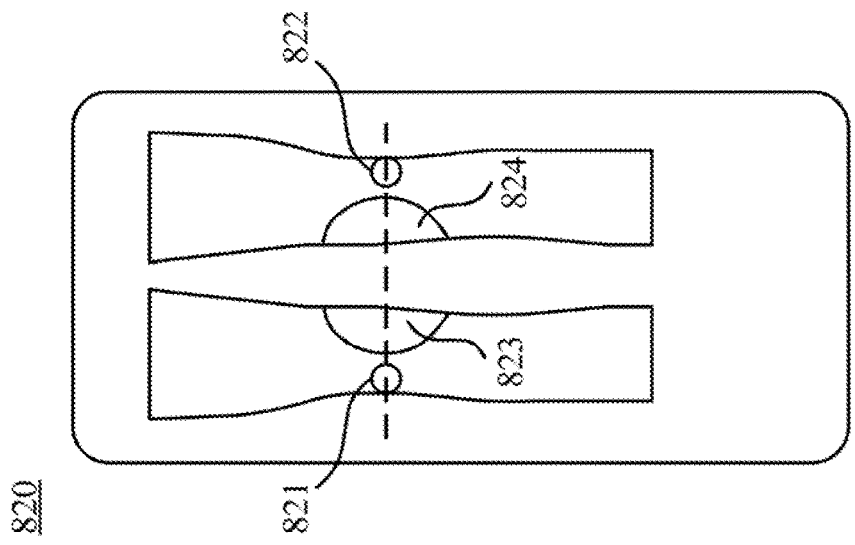

As shown in FIG. 8A, the portable device may display center of foot pressure information 811 and 812 of a users sole through a user interface 810. A center of foot pressure of the users left foot is close to a front end of the foot, and a center of pressure of the users right foot is close to left front side. The portable device (or the analysis engine) may generate center of gravity correction advices 813 and 814 according to the center of foot pressure information 811 and 812 to suggest that the user adjust centers of gravity of the feet to appropriate positions. Moreover, the portable device may also display a foot progression angle 815, a step length 817, a step width 816 and gait information 818 through the user interface 810. As shown in FIG. 8A, the user is going upstairs at the moment. The user's foot progression angle is 60 degrees (defined as an angle between left/right foot and a direction of progression, and an angle of a toe-out gait is positive), a step width is 45 cm, and a step length is 30 cm. In another embodiment, the gait information 818 may not be displayed on the user interface 810.

Figure 8B:
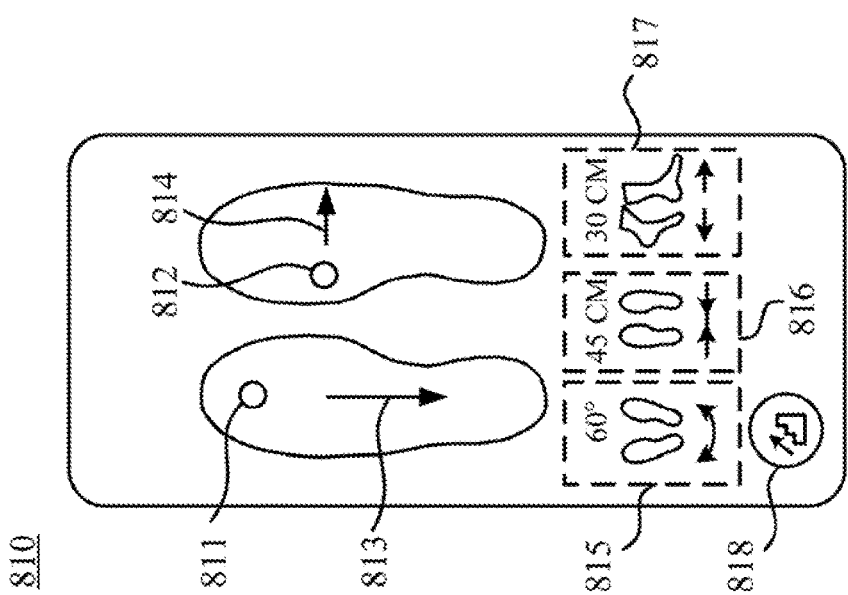

As shown in FIG. 8B, the portable device may display distribution information of knee force through a user interface 820. Areas 821 and 822 indicate that knee force in these areas may be harmful to knee joints, an area 823 indicates that knee force in the area is in a good range, and an area 824 indicates that knee force in the area is in an average range. As a result, the user can adjust to a gait that is beneficial to the knee joints according to current distribution information of knee force displayed on the user interface 820 and the gait correction advice.

As shown in FIG. 8C, the portable device may display knee angle information through a user interface 830. A knee angle of the user's left foot is shown as a point 831, and a knee angle of the user's right foot is shown as a point 832. As a result, the user can adjust to a gait that is beneficial to the knee joints according to the knee angle information and the gait correction advice displayed on the user interface 830 immediately.

As shown in FIG. 8D, the portable device may display distribution information of average foot pressure through a user interface 840. An area 841 indicates an area with largest foot pressure, and an area 842 indicates an area with secondary foot pressure. Areas except for the areas 841 and 842 are areas with relatively low foot pressure. As a result, the user refers to the distribution of average foot pressure when walking to adjust the gait. It should be noted that the distribution information of average foot pressure may be divided into several areas according to pressure scale, and not be limited to the present embodiment.

Figure 8E:
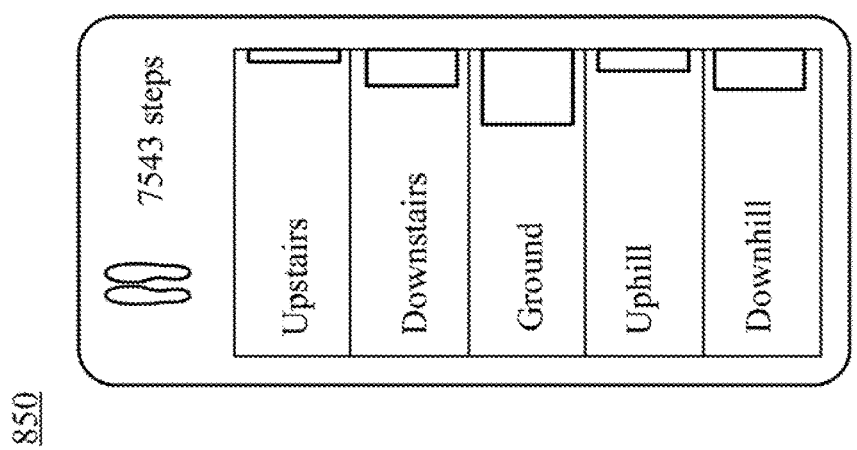

As shown in FIG. 8E, the portable device may display activity history information through a user interface 850. The user interface 850 displays the user's step count is 7543 steps and a ratio of different gait information (including situations of going upstairs, going downstairs, ground, uphill and downhill). As a result, the user can refer to the activity history information to adjust activity pattern (e.g., climbing stairs as frequently as possible to achieve a purpose of consuming excess energy).

In practice, the pressure sensing unit may be a pressure sensor, and the inertial sensing unit may be an inertial sensor. The portable devices 130 and 630 may be a notebook, a tablet personal computer and so on. However, the present disclosure is not limited to the exemplary implementations. The analysis engines 450 and 640 may be implemented as computers.

Figure 9:
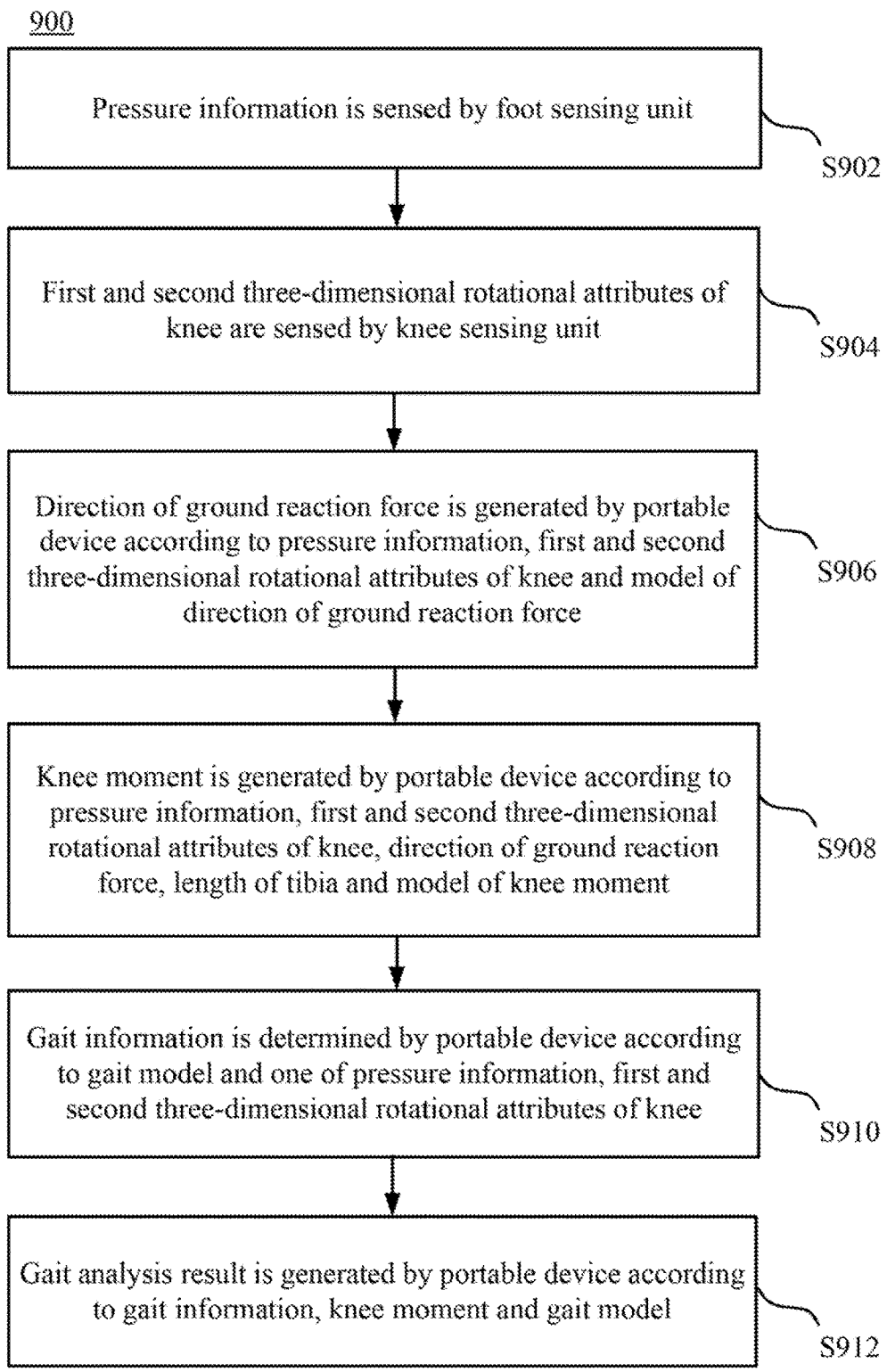
FIG. 9 is a flow chart of a gait analysis method according to an embodiment of the present disclosure.

FIG. 9 is a flow chart of a gait analysis method 900 according to an embodiment of the present disclosure. The gait analysis method 900 includes steps S902-S912, and the gait analysis method 900 can be applied to the gait analysis systems 100 and 400 as shown in FIGS. 1 and 4. However, those skilled in the art should understand that the mentioned steps in the present embodiment are in an adjustable execution sequence according to the actual demands except for the steps in a specially described sequence, and even the steps or parts of the steps can be executed simultaneously. Specific implementation is described as aforementioned, and is not repeated herein. Implementation and operation of the foot sensing unit, the knee sensing unit and the portable device are similar to the above description, and are not repeated herein.

In step S902, pressure information is sensed by a foot sensing unit.

In step S904, a first three-dimensional rotational attribute of knee and a second three-dimensional rotational attribute of knee are sensed by a knee sensing unit.

In step S906, direction of ground reaction force is generated by a portable device according to the pressure information, the first three-dimensional rotational attribute of knee, the second three-dimensional rotational attribute of knee and a model of direction of ground reaction force.

In step S908, a knee moment is generated by the portable device according to the pressure information, the first three-dimensional rotational attribute of knee, the second three-dimensional rotational attribute of knee, the direction of ground reaction force, a length of tibia and a model of knee moment.

In step S910, gait information is determined by the portable device according to a gait model and one of the pressure information, the first three-dimensional rotational attribute of knee and the second three-dimensional rotational attribute of knee.

In step S912, a gait analysis result is generated by the portable device according to the gait information, the knee moment and the gait model.

Through the above embodiments, the present disclosure can sense pressure data and angle data of a user's foot and knee, and generate an analysis result and an advice for adjustment after analysis. The portable device held by the user can display the analysis result and the advice for adjustment, and therefore the user can understand whether the current gait is harmful to health immediately and adjust to a gait that is beneficial to health according to the advice for adjustment.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A gait analysis system, comprising:
   a foot sensing unit, comprising:
   at least one pressure sensing unit, configured to sense a pressure information;
   a knee sensing unit, comprising:
   a first inertial sensing unit, configured to sense a first three-dimensional rotational attribute of knee; and
   a second inertial sensing unit, configured to sense a second three-dimensional rotational attribute of knee; and
   a portable device, configured to generate a direction of ground reaction force according to the pressure information, the first three-dimensional rotational attribute of knee, the second three-dimensional rotational attribute of knee and a model of direction of ground reaction force, to generate a knee moment according to the pressure information, the first three-dimensional rotational attribute of knee, the second three-dimensional rotational attribute of knee, the direction of ground reaction force, a length of tibia and a model of knee moment, to determine a gait information according to a gait model and one of the pressure information, the first three-dimensional rotational attribute of knee and the second three-dimensional rotational attribute of knee, and to generate a gait analysis result according to the gait information, the knee moment and the gait model.

2. The gait analysis system of claim 1, wherein the portable device display the gait analysis result through a user interface, and the gait analysis result comprises a distribution information of knee force.

3. The gait analysis system of claim 1, wherein the first three-dimensional rotational attribute of knee comprises a tibia angle, the second three-dimensional rotational attribute of knee comprises a femur angle, the portable device is further configured to generate a knee angle information according to the tibia angle and the femur angle, and to display the knee angle information through a user interface.

4. The gait analysis system of claim 3, wherein the portable device stores a foot parameter, and is further configured to determine a sequence of the knee moment and the knee angle information for determination according to the foot parameter and the gait information to generate a gait adjustment advice, and to display the gait adjustment advice through the user interface.

5. The gait analysis system of claim 1, wherein the foot sensing unit further comprises at least one inertial sensing unit that is configured to sense an acceleration and an angle of foot, the portable device is further configured to generate a foot progression angle, a step length and a step width according to the acceleration and the angle of foot.

6. The gait analysis system of claim 1, wherein the model of direction of ground reaction force comprises a model of center of pressure, the portable device is further configured to generate a center of foot pressure information according to the pressure information and the model of center of pressure, and to display the center of foot pressure information through a user interface.

7. The gait analysis system of claim 6, wherein the portable device is further configured to generate a center of gravity correction advice according to the center of foot pressure information, and to display the center of gravity correction advice through the user interface.

8. The gait analysis system of claim 1, wherein the portable device is further configured to receive the model of direction of ground reaction force, the model of knee moment and the gait model from an analysis engine, the analysis engine builds the model of direction of ground reaction force, the model of knee moment and the gait model through machine learning.

9. The gait analysis system of claim 1, further comprising:
a support unit, comprising a support pressure sensing unit and a support inertial sensing unit and configured to generate a support pressure data and a support angle data, wherein the support unit and the foot sensing unit are further configured to generate a relative position of the foot sensing unit and the support unit, and the portable device is further configured to calculate a support weight according to the support pressure data and the support angle data, and to display the support weight and the relative position through a user interface.

10. A gait analysis system, comprising:
a foot sensing unit, comprising:
at least one pressure sensing unit, configured to sense a pressure information;
a knee sensing unit, comprising:
a first inertial sensing unit, configured to sense a first three-dimensional rotational attribute of knee; and
a second inertial sensing unit, configured to sense a second three-dimensional rotational attribute of knee; and
an analysis engine, configured to build a model of direction of ground reaction force, a model of knee moment and a gait model through machine learning; and
a portable device, configured to receive the pressure information, the first three-dimensional rotational attribute of knee and the second three-dimensional rotational attribute of knee from the foot sensing unit and the knee sensing unit, and to send the pressure information, the first three-dimensional rotational attribute of knee and the second three-dimensional rotational attribute of knee to the analysis engine;
wherein the analysis engine is configured to generate a direction of ground reaction force according to the pressure information, the first three-dimensional rotational attribute of knee, the second three-dimensional rotational attribute of knee and the model of direction of ground reaction force, to generate a knee moment according to the pressure information, the first three-dimensional rotational attribute of knee, the second three-dimensional rotational attribute of knee, the direction of ground reaction force, a length of tibia and the model of knee moment, to determine a gait information according to the gait model and one of the pressure information, the first three-dimensional rotational attribute of knee and the second three-dimensional rotational attribute of knee, to generate a gait analysis result according to the gait information, the knee moment and the gait model, and to send the gait analysis result to the portable device.

11. The gait analysis system of claim 10, wherein the first three-dimensional rotational attribute of knee comprises a tibia angle, the second three-dimensional rotational attribute of knee comprises a femur angle, the analysis engine is further configured to generate a knee angle information according to the tibia angle and the femur angle, and to send the knee angle information to the portable device, and the portable device is further configured to display the knee angle information through a user interface.

12. The gait analysis system of claim 10, wherein the foot sensing unit further comprises at least one inertial sensing unit that is configured to sense an acceleration and an angle of foot, the analysis engine is further configured to generate a foot progression angle, a step length and a step width according to the acceleration and the angle of foot.

13. The gait analysis system of claim 10, wherein the model of direction of ground reaction force comprises a model of center of pressure, the analysis engine is further configured to generate a center of foot pressure information according to the pressure information and the model of center of pressure, and to send the center of foot pressure information to the portable device, and the portable device is further configured to display the center of foot pressure information through a user interface.

14. The gait analysis system of claim 10, further comprising:
a support unit, comprising a support pressure sensing unit and a support inertial sensing unit and configured to generate a support pressure data and a support angle data, wherein the support unit and the foot sensing unit are further configured to generate a relative position of the foot sensing unit and the support unit and to send the relative position to the analysis engine, the analysis engine is further configured to calculate a support weight according to the support pressure data and the support angle data, and to send the support weight to the portable device, and the portable device is further configured to display the support weight and the relative position through a user interface.

15. A gait analysis method, comprising:
by a foot sensing unit, sensing a pressure information;
by a knee sensing unit, sensing a first three-dimensional rotational attribute of knee and a second three-dimensional rotational attribute of knee;
by a portable device, generating a direction of ground reaction force according to the pressure information, the first three-dimensional rotational attribute of knee, the second three-dimensional rotational attribute of knee and a model of direction of ground reaction force;
by the portable device, generating a knee moment according to the pressure information, the first three-dimensional rotational attribute of knee, the second three-dimensional rotational attribute of knee, the direction of ground reaction force, a length of tibia and a model of knee moment;
by the portable device, determining a gait information according to a gait model and one of the pressure information, the first three-dimensional rotational attribute of knee and the second three-dimensional rotational attribute of knee; and
by the portable device, generating a gait analysis result according to the gait information, the knee moment and the gait model.

16. The gait analysis method of claim 15, further comprising:
by the portable device, generating a knee angle information according to a tibia angle and a femur angle, wherein the first three-dimensional rotational attribute of knee comprises the tibia angle, the second three-dimensional rotational attribute of knee comprises the femur angle; and
by a user interface of the portable device, displaying the knee angle information.

17. The gait analysis method of claim 15, further comprising:
by at least one inertial sensing unit of the foot sensing unit, sensing an acceleration and an angle of foot;
by the portable device, generating a foot progression angle, a step length and a step width according to the acceleration and the angle of foot;
by the portable device, generating a center of foot pressure information according to the pressure information and a model of center of pressure of the model of direction of ground reaction force; and
by a user interface of the portable device, displaying the center of foot pressure information.

18. The gait analysis method of claim 15, further comprising:
by an analysis engine, building the model of direction of ground reaction force, the model of knee moment and the gait model through machine learning; and
by the portable device, receiving the model of direction of ground reaction force, the model of knee moment and the gait model from the analysis engine.

19. The gait analysis method of claim 15, further comprising:
by a support unit, generating a support pressure data and a support angle data, wherein the support unit comprises a support pressure sensing unit and a support inertial sensing unit;
by the support unit and the foot sensing unit, generating a relative position of the foot sensing unit and the support unit;
by the portable device, calculating a support weight according to the support pressure data and the support angle data; and
by a user interface of the portable device, displaying the support weight and the relative position.

* * * * *